United States Patent [19]

Sundström et al.

[11] 4,341,948

[45] Jul. 27, 1982

[54] APPARATUS WITH BUILT-IN HEATING DEVICE FOR DISINFECTING CONTACT LENSES

[75] Inventors: Staffan Sundström; Tore Herlestam, both of Helsingborg, Sweden

[73] Assignee: AB Leo, Helsingborg, Sweden

[21] Appl. No.: 230,704

[22] Filed: Feb. 2, 1981

[30] Foreign Application Priority Data

Feb. 4, 1980 [SE] Sweden ............................. 80009250

[51] Int. Cl.³ ........................................... F27D 11/02
[52] U.S. Cl. .................................. 219/521; 219/439; 219/386; 219/433; 219/441; 422/307
[58] Field of Search .............. 219/328, 386, 430, 433, 219/439, 441, 438, 442, 521; 422/38, 56, 117, 307; 126/388

[56] References Cited

U.S. PATENT DOCUMENTS

| | | | |
|---|---|---|---|
| 3,998,950 | 12/1976 | Glorieux | 422/117 |
| 4,158,126 | 6/1979 | Seitz | 219/439 |
| 4,178,449 | 12/1979 | Bowen | 219/439 |
| 4,270,039 | 5/1981 | Houser | 219/439 |

*Primary Examiner*—Volodymyr Y. Mayewsky
*Attorney, Agent, or Firm*—Gordon W. Hueschen

[57] ABSTRACT

Apparatus for disinfecting contact lenses by heating, comprising a reservoir designed for holding a liquid and having a tight lid together with a heating device for heating of liquid therein, wherein the reservoir comprises a raised middle part or bridge for dividing said reservoir into two separate chambers or wells, and having a built-in heating device for direct heating of the liquid in said chambers.

10 Claims, 8 Drawing Figures

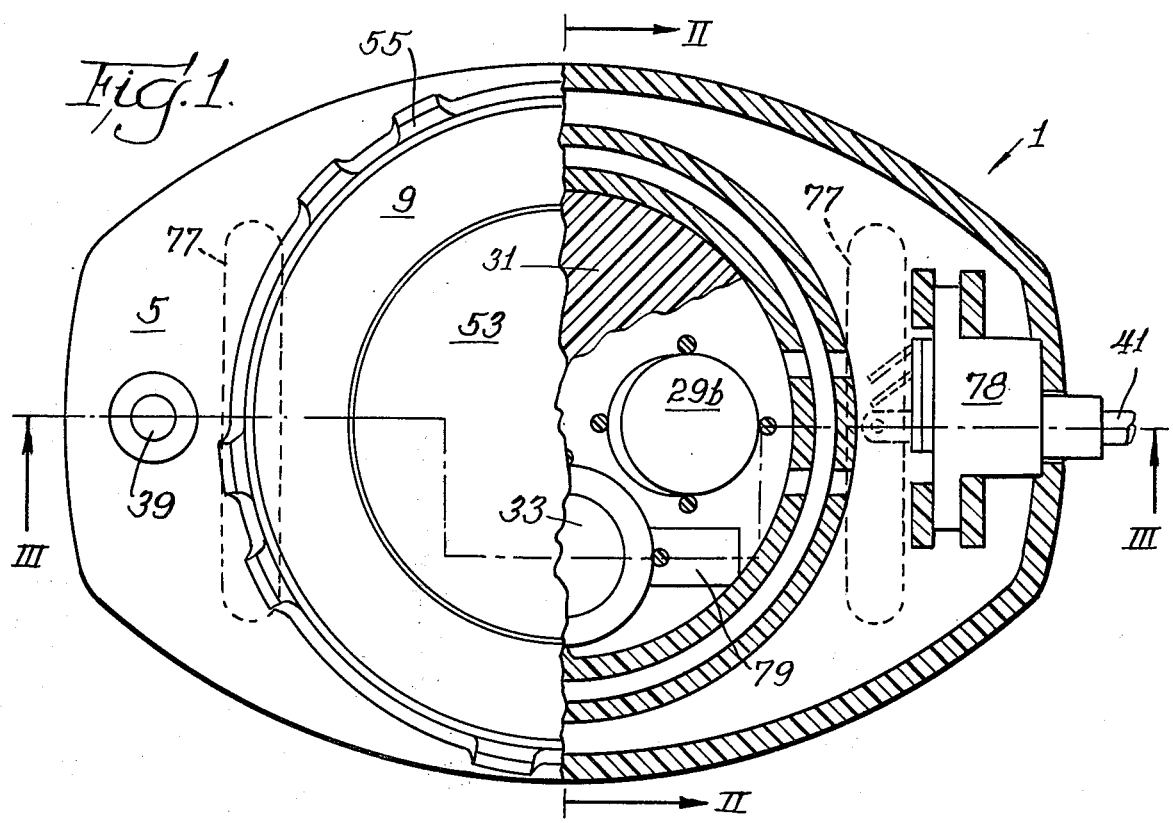
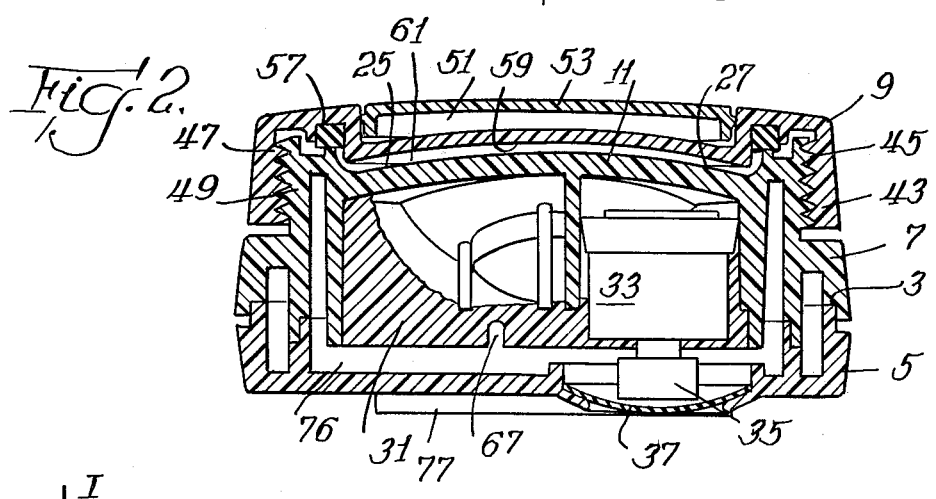
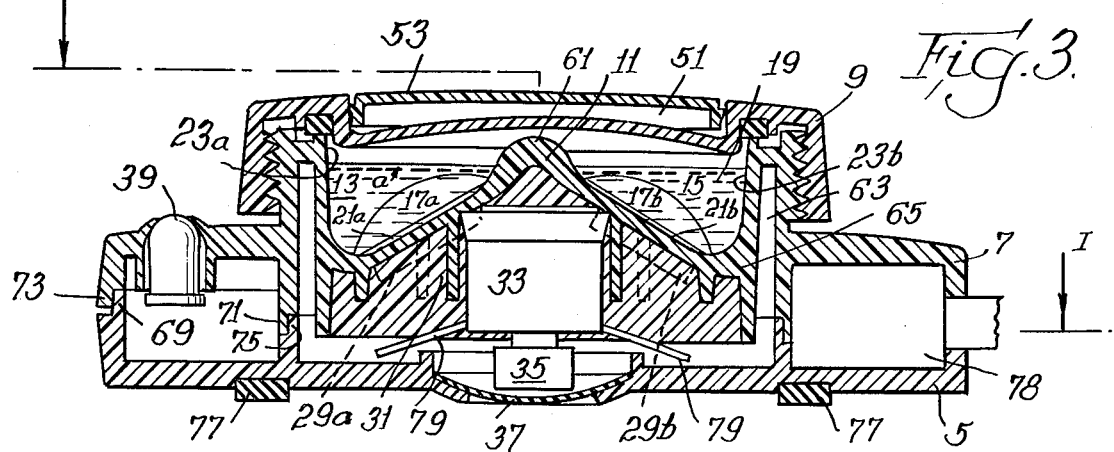

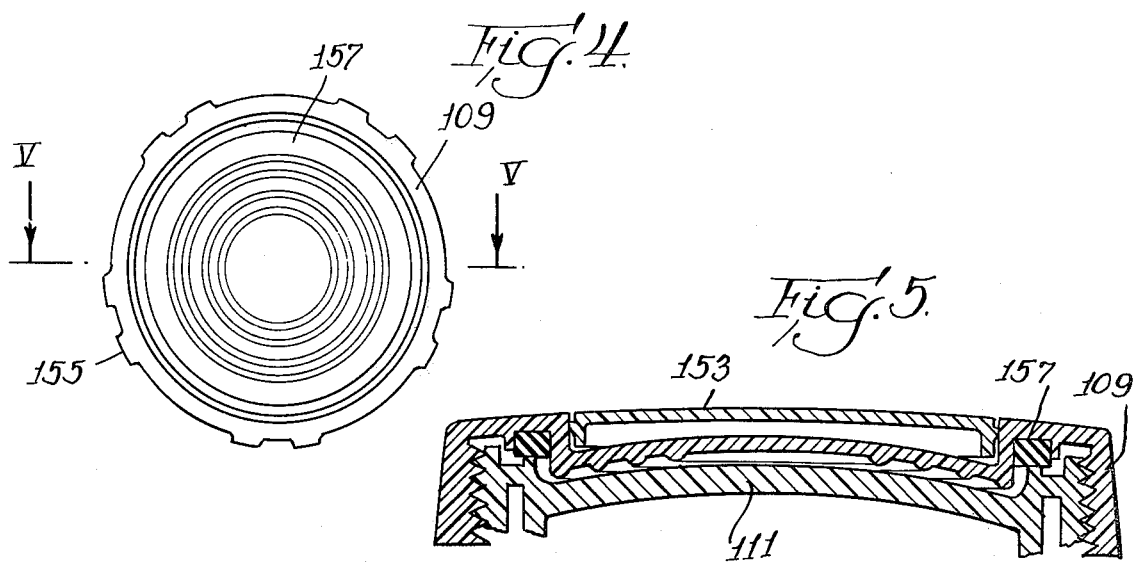
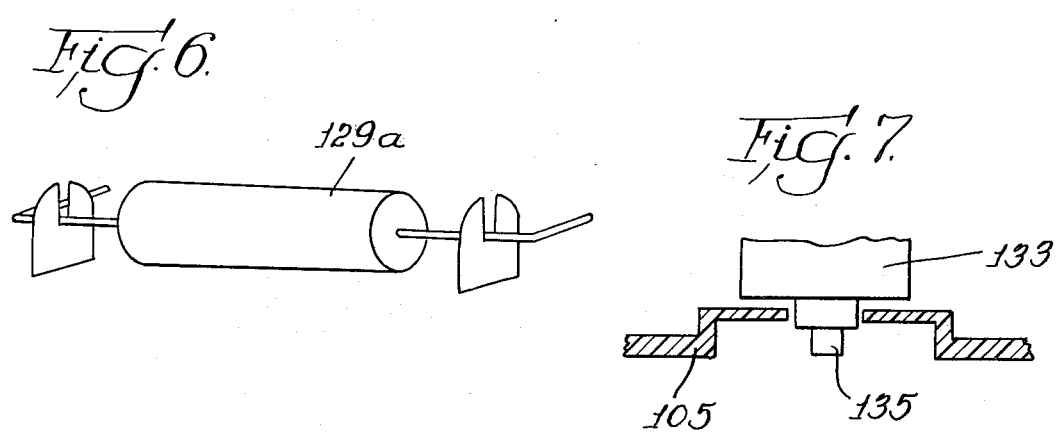
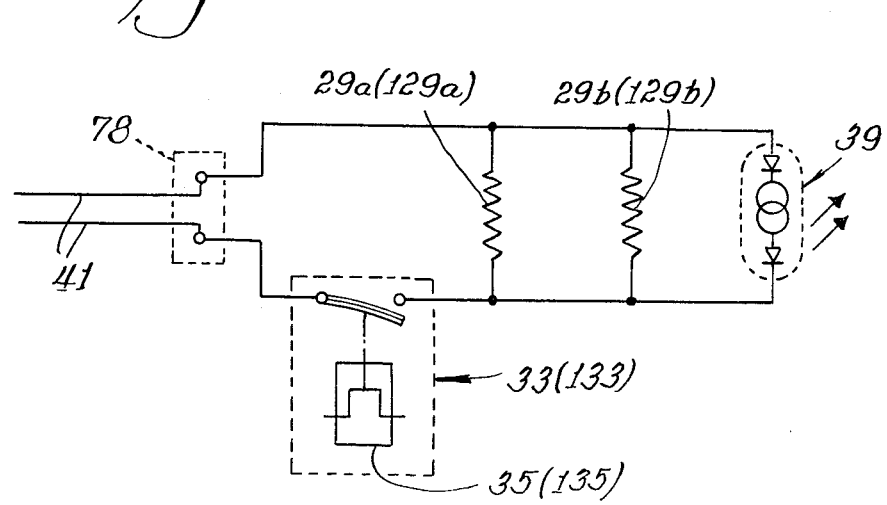

APPARATUS WITH BUILT-IN HEATING DEVICE FOR DISINFECTING CONTACT LENSES

FIELD OF THE INVENTION

The present invention relates to an apparatus for disinfecting contact lenses by heating, comprising a reservoir designed to hold a liquid, a heating device for heating of the liquid, and having a tight lid.

BACKGROUND OF INVENTION AND PRIOR ART

Soft contact lenses are usually disinfected either by short-term heating at a temperature over 80° in an isotonic sodium chloride solution or by treatment at room temperature with such solution containing disinfecting chemical agents.

Disinfecting by heating is more advantageous from several points of view. A more reliable result is reached, and at the same time the risk of accumulating contamination, which might harm the eyes, in the lens material is avoided. This is especially important since disinfection of the lenses must normally be carried out once every 24 hours.

The heating devices for contact lenses, which are on the market today, operate according to one of the following basic principles.

A reservoir, in which the lenses are kept in isotonic sodium chloride solution, is lowered into a water-bath which is then heated to over 80° C. When the water in the water-bath has evaporated, the temperature rises rapidly, whereupon a thermoswitch turns off the current at a predetermined temperature. When the apparatus has cooled, the lens receptacle may be taken out and the lenses worn.

According to another procedure the lens receptacle, which in principle may be of the same design as the one in the above "water-bath method", is placed in a device where the receptacle is heated by direct transport of heat from a heated surface in the apparatus. Here, too, high temperatures in the heat source are used so that the lenses in an isotonic sodium chloride solution are heated to over 80° C. By means of a thermoswitch, the temperature in the lens receptacle is adjusted so as to prevent boiling. After cooling, the receptacle and the lenses may be taken out.

The lens receptacle of above-mentioned design may be a jar with a lid or a closed box in which the lens is fastened in a holder designed especially for this purpose, the design being such that while being heated the lens is in contact with the sodium chloride solution. The lens receptacle may be so designed that both lenses share a volume of liquid or so that each lens has its own volume of liquid.

INVENTION

The present invention is intended to eliminate the disadvantages of known techniques and the inconvenience of practical handling. In the present invention the lens receptacle itself, with its tight-fitting lid, is so designed that it has a built-in heating device. The receptacle is, by means of a raised middle part or bridge, separated into two separate chambers or wells, one for each lens and, in connection with these chambers, the heating device is arranged for direct heating of the disinfecting liquid therein.

The raised middle part or bridge between the two chambers contains at least one hollow recess, or relatively lower zone, which enables liquid to communicate between the chambers in such a way that, when a lens is taken out of one chamber, liquid can be conveniently transferred to the other chamber, so that on handling the apparatus spillage is avoided.

To make it easier to remove the lenses from the chambers of the receptacle, the raised middle part or bridge is designed so that it comprises sloping side-walls and widens toward the bottom. When the apparatus is used, the disinfecting liquid should naturally be added in such amount that both lenses in both chambers are completely covered. To minimize the amount of liquid needed, the exterior side-walls of said chambers are steep and, preferably, mainly vertical. The raised middle part or bridge is, preferably, made with two hollows, one at each end of the bridge.

The apparatus according to the invention is preferably equipped with a heating device in thermal contact with each of the side-walls for direct heating of the disinfecting liquid in the corresponding chamber. The heating devices are preferably of the electric resistance type, for which reason the apparatus should be equipped with a thermostat which, when the desired temperature is reached in the disinfecting liquid, automatically turns off the supply of current to said resistance. The thermostat is preferably so adjusted that the supply of current is turned off when the temperature in the disinfecting liquid has risen to about 85° C.

To avoid confusion between the two contact lenses which are normally used, and which are usually adjusted to the individual correction of the sharpness of vision on the right or the left eye, the interior of the lid is so designed in relation to the upper side of the bridge that shifting of a lens from one chamber to the other is not possible when the lid is in place.

To minimize waste of heat to the surroundings, the receptacle as well as the lid is equipped with air cores for heat insulation of the directly heated parts of the apparatus. The lid is preferably fixedly but removably secured to the receptacle by thread cuttings.

The heating device of the apparatus is preferably operated from a twelve-volt source of current, whereby the risk of accident by using the apparatus is minimized. Furthermore, the apparatus may in this case be connected to usual twelve-volt systems commonly to be found in cars, boats, and caravans. For switching on to the mains, a standard transformer may be used.

Those parts of the apparatus which are exposed to liquid and to the surroundings are preferably made of heat- and liquid-resistant plastic, for instance polycarbonate. Thereby the problems of corrosion, which are often to be found with the well-known techniques mentioned at the beginning of this description, are avoided. Further, the apparatus may be of a small size and low weight and, with the lid secured in place, may be handled freely and kept in a pocket, for example, with disinfection solution and contact lenses therein. This is important in case the wearer of the contact lenses is travelling and desires to carry with him the necessary aids for care of the contact lenses.

BRIEF DESCRIPTION OF DRAWINGS

The invention will now be described with respect to a not limiting exemplifying design in connection with the enclosed drawings.

FIG. 1—is a view from above of a section along the line I—I in FIG. 3.

FIG. 2—is a vertical section along the line II—II in FIG. 1,

FIG. 3—is a vertical section along the line III—III in FIG. 1,

FIG. 4—is a bottom view of the interior of another form of lid according to the invention, and FIG. 5—is a cross-sectional view along the line V—V of FIG. 4 and also shows the bridge 11 of FIG. 2, FIG. 6—shows another form of resistance heater which may be incorporated into the device of the invention, and FIG. 7—shows another form of thermostat activating or return button means which may be incorporated into a device of the invention, FIG. 8—is a diagram showing the circuitry involved in a preferred form of device according to the invention.

DETAILED DESCRIPTION OF THE INVENTION

The apparatus of the drawing is generally shown at 1 and fundamentally comprises a receptacle 3 with a bottom part 5 and an upper part 7 in connection therewith, as well as a lid 9. Details of these main parts and their function will be further described below.

The receptacle 3, i.e., its upper part 7, is equipped with a centrally raised middle portion or bridge 11, which divides the central circular part of the upper area 7 into two chambers 13 and 15, which are designed for holding disinfecting liquid 19 at a level indicated by the arrows a. Each of the chambers 13 and 15 containing this disinfecting liquid is designed to hold a contact lens 17a and 17b, respectively, immersed in the liquid.

The bridge 11 is equipped with sloping side-walls 21a and 21b, which on reaching the bottom of the chambers merge into steep side-walls 23a and 23b (FIG. 3). As is especially clear from FIG. 2, the bridge 11 is, when seen as a longitudinal section, formed with a downward slope towards its ends, whereby two hollows 25 and 27 are formed, the function of which will be described hereinafter.

Inside the sloping side-walls 21a and 21b in upper part 7 are located heaters 29a and 29b (FIG. 3) in the form of power resistors (positive temperature coefficient resistors, e.g., Murata PTH), which are imbedded in a suitable material 31, preferably epoxy plastic, for instance plastic-padding. Said material preferably has good thermal conductivity and also high electrical insulation characteristics. It preferably also emits heat only slowly, thereby prolonging the time during which the temperature within the chambers is maintained at a suitable level, e.g., 80° C. These heaters 29a and 29b are operated in connection with a thermostat 33 (Elmwood, 90 or 95 C), located under the raised middle part 11 and to either side of the heaters and having attached soldering tags 79 (FIGS. 1 and 3), and below equipped with a return button 35 which can be operated from the outside (FIG. 3). To make it water-tight, this return button 35 may be covered by a protective membrane 37, which can be made of rubber or the like (FIG. 3).

In the receptacle, i.e., the upper part 7, a light-emitting diode 39, e.g., NSL 4944 from National Semiconductor, is built-in to the left in FIG. 3, while at the other end of the receptacle 3 a cable 41 is connected, as shown in FIG. 1.

As is shown in FIG. 1 and FIG. 3, the lid 9 is circular cylindric and equipped with a flange 43 pointing downwardly with inside thread cuttings 45. The inside thread cuttings of the lid co-operate with outside thread cuttings 47 (FIG. 2) arranged on an upwardly-pointing circular cylindric projecting portion of the upper parts 7 of the receptacle 3. The lid 9, as shown, is equiped with an air core 51 limited by a central groove in the lid and a press-on plate 53, which is necessary only for production convenience.

Further, the lid is equipped with projecting grips 55 (FIG. 1) to facilitate screwing on and off of the lid. For tightening, the inside of the lid is equipped with a circular washer 57 with a rectangular cross section arranged in a circular groove inside the lid (FIG. 2).

As is seen in FIG. 2, the inner contour 59 of the lid is so distanced with respect to the upper surface 61 of the raised middle part or bridge 11 that the contact lenses 17a and 17b, when placed in the chambers 13 and 15, cannot be transferred from one chamber to the other when the lid 9 is screwed in place.

The upper part 7 of the receptacle is equipped with circular air core 63, limited on the inside by a downwardly-pointing circular flange 65 (FIG. 3). Further, a groove 67 is arranged in the upper part 7 for a through connection of electric components for connecting resistors, theremostat, and light-emitting diode.

The lower part 5 is equipped with upwardly-pointing flanges 69 and 75, which co-operate with corresponding downwardly-pointing flanges 73 and 71, respectively, arranged on the upper part 7 (FIG. 3). Between the lower part 5 and the upper part 7 is located air core 76 (FIG. 2). The lower part 5 is in addition equipped on the underside with feet 77, for instance of rubber or plastic. As shown, two transversely-arranged feet 77 are present on the bottom of the lower part 5 but the exact size, shape, and location of the feet is not critical. For example, four (4) pointed plastic feet may be molded into the lower part 5 and may be suitably located at the approximate ends of feet 77 as presently indicated in FIG. 1.

The foregoing-described apparatus is constructed of heat-resistant plastic, e.g., a polycarbonate. Suitable polycarbonate products are available under the trade names Makrolon 2808 from Bayer AG, Germany, and Lexan 144 R or 164 R from General Electric, USA. The apparatus functions as follows:

To prepare the apparatus for use, chambers 13 and 15 are filled with disinfecting liquid, preferably isotonic sodium chloride solution, to the level indicated in FIG. 3 by the arrows a. The contact lenses 17a and 17b are then placed, for instance, in the position indicated in FIG. 3, whereby the contact lens for the left eye is placed in the space facing the light-emitting diode 39, whereas the contact lens for the right eye is placed in the opposite chamber 15.

The apparatus is now connected to a twelve-volt source via wire 41, which is connected to the supply socket 78 (Marushin MJ 180), located so as to be accessible from the exterior of the device, whereafter the return or activating button 35 of the thermostat 33 must be pressed. When the apparatus is switched on, the light-emitting diode 39 is lit to indicate that the apparatus is in the heating stage. After a certain period, for instance 15 to 30 minutes, the isotonic sodium chloride solution 19 in chambers 13 and 15 will have reached a temperature of about 85° C., whereupon the thermostat 33 switches off the current supply so that slow cooling takes place. Heat insulation is provided by air cores 51, 63, and 76 surrounding the heated parts of the apparatus, whereby (1) the amount of energy for the heating is minimized, and (2) cooling takes place at a relatively slow rate so that the temperature will remain above 80° C. for at least ten minutes.

After cooling, lid 9 is unscrewed and contact lenses 17a and 17b may readily be removed from chambers 13 and 15, respectively, to be put into use by the wearer. Due to the design of the chambers 13 and 15 (FIG. 3), the advantage of an adequate liquid depth can be achieved despite the relatively small amount of liquid employed, and each lens may readily be removed from its chamber. Because of light-emitting diode 39 the user of the apparatus may readily distinguish between the different lenses, so that the left and the right lenses are not confused. Due to the afore-mentioned design and proximity of the interior 59 of lid 9 in relation to the uppermost surface 61 of the raised middle or bridge portion 11, unintentional transfer of a contact lens from one chamber to the other is precluded.

In FIGS. 4–7 are shown alternative embodiments of the invention, wherein the corresponding elements are correspondingly numbered in the 100 series, including a ribbed lid for holding lenses more securely within their respective wells or chambers, alternative resistance heater means, and alternative thermostat activating or return button means, which may be employed in place of the same elements as shown in FIGS. 1–3 and described in the foregoing, and in which embodiments the elements perform exactly the same function as in the embodiments of FIGS. 1–3. The resistor in FIG. 6 as shown is a Dale power resistor, 47Ω.

The apparatus according to the invention has several important advantages, of which the following are representative:

Because the apparatus is constructed in one piece with a built-in heating device, it is easy to handle and may readily be taken along when travelling. The design of the liquid chambers 13 and 15 simplifies removal of the contact lenses, and spillage is avoided because of the hollows 25 and 27 of the bridge portion. Accordingly, when the contact lens in one chamber is removed after disinfection, the level of the liquid in the corresponding chamber may rise but, since liquid may flow over into the other chamber, spillage onto the surrounding edge of the receptacle is avoided. Because of water-tight screw-on lid 9, the receptacle may readily be transported with both disinfecting liquid and contact lenses in place therein. The thermostatic control and the water-tightness of the receptacle prevent the risk of overheating, whereas at the same time the overall design of the apparatus and the included air cores prevent any essential heating of the exterior of the apparatus. Since those parts of the apparatus which are in contact with the disinfecting liquid are constructed of plastic, corrosion is avoided and cleaning of the apparatus is simplified.

As shown in FIG. 8 the electrical circuitry involved in the device of the present invention includes wire or cable 41, connected to supply socket 78, which is preferably a Marushin MJ 180. One side of the wiring from socket 78 goes through soldering tag 79 to the thermostat 33, which is preferably a thermoswitch Elmwood 90 or 95C, which in turn is connected to the two power resistors 29a and 29b or 129a and 129b and as well to the light-emitting diode 39 which are all in parallel and in turn connected to the other wire leading back to the supply socket 78 so that no current can pass into the heating elements or the diode unless permitted by the thermostat 33.

It should be noted that the invention is not to be limited to the exact details, design, materials, or elements set forth in the foregoing, since these may be modified in many respects by one skilled in the art without departure from the scope of the invention.

We claim:

1. Apparatus for disinfecting contact lenses by heating, comprising a reservoir adapted for holding a liquid and having a tight lid together with a heating device for heating of liquid therein, wherein the reservoir comprises a raised middle part or bridge for dividing said reservoir into two separate chambers or wells, said raised middle part being equipped with at least one hollow recess at its top, which enables liquid to communicate between the chambers in such a way that spillage of liquid is avoided when a lens is removed from either of said chambers, said raised middle part having side-walls, and having a built-in heating device for heating of the liquid in said chambers, said heating device being located adjacent to each of said side-walls for heating of liquid in each of said chambers of said reservoir, said heating device being of the electric resistance type.

2. Apparatus according to claim 1, wherein the raised middle part has sloping side-walls and widens toward the bottom, to faciliate removal of lenses in contact with these side-walls.

3. Apparatus according to claim 2, wherein said chambers have step outer side-walls, so that the amount of liquid required to cover each lens is minimized.

4. Apparatus according to claim 1, 2, or 3, wherein the raised middle part is equipped at its top with two hollow recesses one at each end.

5. Apparatus according to claim 1, 2, or 3, wherein a thermostat is present which, when the lquid has reached the desired temperature, is adapted to cut off the flow of current to the resistors.

6. Apparatus according to claim 1, 2, or 3, wherein the interior of the lid is so related to the top of the middle part that, when the lid is on, a transfer of a lens from one chamber to the other is impossible.

7. Apparatus according to claim 2 or 3, wherein the reservoir and the lid are equipped with air cores to insulate the heated part of the apparatus.

8. Apparatus according to claim 6, wherein the lid and reservoir are so constructed as to be connected by means of threads.

9. Apparatus according to claim 8, wherein a light-emitting diode is also present and wherein the thermostat is also adapted to cut off the flow of current to said diode.

10. Apparatus according claim 1, 2 or 3, wherin the heating device is imbedded in plastic padding having good thermal conductivity and high electrical insulation characteristics.

* * * * *